US012673220B2

(12) United States Patent
Lim et al.

(10) Patent No.: US 12,673,220 B2
(45) Date of Patent: Jul. 7, 2026

(54) CONVERSION DEVICE FOR CONVERTING TREATMENT BEAM FOR TREATING LESION OF SUBJECT

(71) Applicants: NATIONAL CANCER CENTER, Goyang-si (KR); RAPHARAD INC., Seoul (KR); INDUSTRY-ACADEMIC COOPERATION FOUNDATION, YONSEI UNIVERSITY, Seoul (KR); SAMSUNG LIFE PUBLIC WELFARE FOUNDATION, Seoul (KR)

(72) Inventors: Young Kyung Lim, Paju-si (KR); Myeong Soo Kim, Suwon-si (KR); Kyeong Yun Park, Goyang-si (KR); Do Hyeon Kim, Goyang-si (KR); Sang Soo Kim, Seoul (KR); Hak Soo Kim, Goyang-si (KR); Jong Hwi Jeong, Seoul (KR); Se Byeong Lee, Goyang-si (KR); Dong Ho Shin, Suwon-si (KR); Joo Young Kim, Seoul (KR); Tae Hyun Kim, Seoul (KR); Seong Ho Moon, Seoul (KR); Yang-Gun Suh, Seoul (KR); Hojin Kim, Seoul (KR); Kwanghyun Jo, Seoul (KR)

(73) Assignees: NATIONAL CANCER CENTER, Goyang-si (KR); RAPHARAD INC., Seoul (KR); INDUSTRY-ACADEMIC COOPERATION FOUNDATION, YONSEI UNIVERSITY, Seoul (KR); SAMSUNG LIFE PUBLIC WELFARE FOUNDATION, Seoul (KR)

( * ) Notice: Subject to any disclaimer, the term of this patent is extended or adjusted under 35 U.S.C. 154(b) by 196 days.

(21) Appl. No.: 18/290,618

(22) PCT Filed: Jun. 23, 2022

(86) PCT No.: PCT/KR2022/008935
§ 371 (c)(1),
(2) Date: Jan. 19, 2024

(87) PCT Pub. No.: WO2023/003189
PCT Pub. Date: Jan. 26, 2023

(65) Prior Publication Data
US 2024/0335678 A1 Oct. 10, 2024

(30) Foreign Application Priority Data
Jul. 21, 2021 (KR) ........................ 10-2021-0096045

(51) Int. Cl.
*A61N 5/10* (2006.01)

(52) U.S. Cl.
CPC .... *A61N 5/1042* (2013.01); *A61N 2005/1087* (2013.01); *A61N 2005/1094* (2013.01); *A61N 2005/1095* (2013.01)

(58) Field of Classification Search
None
See application file for complete search history.

(56) References Cited

U.S. PATENT DOCUMENTS

2004/0200983 A1 10/2004 Fujimaki et al.
2010/0187446 A1 7/2010 Dilmanian et al.
(Continued)

FOREIGN PATENT DOCUMENTS

JP 2014-210 A 1/2014
JP 2017-127624 A 7/2017
(Continued)

OTHER PUBLICATIONS

International Search Report issued Sep. 23, 2022 in PCT/KR2022/008935, filed on Jun. 23, 2022, 2 pages.
(Continued)

*Primary Examiner* — Hoon K Song
(74) *Attorney, Agent, or Firm* — Oblon, McClelland, Maier & Neustadt, L.L.P.

(57) ABSTRACT

The present invention relates to a conversion device for converting a treatment beam for treating a lesion of a
(Continued)

subject, comprising: a collimator unit to which the treatment beam is incident and which has a plurality of slits; and a scattering unit that scatters the treatment beam that has passed through the collimator unit.

17 Claims, 14 Drawing Sheets

(56)                    References Cited

U.S. PATENT DOCUMENTS

| | | | |
|---|---|---|---|
| 2015/0085982 A1* | 3/2015 | Willcut | A61N 5/1077 |
| | | | 378/65 |
| 2017/0128739 A1* | 5/2017 | Dilmanian | A61N 5/1084 |
| 2020/0038685 A1* | 2/2020 | Kundapur | G21K 1/025 |

FOREIGN PATENT DOCUMENTS

| | | |
|---|---|---|
| JP | 2018-143859 A | 9/2018 |
| KR | 10-2009-0103780 A | 10/2009 |
| KR | 10-2016-0004145 A | 1/2016 |
| WO | WO 95/01207 A2 | 1/1995 |

OTHER PUBLICATIONS

Korean Office Action issued May 13, 2023 in KR 10-2021-0096045, 11 pages.

Extended European Search Report issued May 8, 2025, in corresponding European Patent Application No. 22846061.4, 10 pages.

G. Cranmer-Sargison et al., "Medical linear accelerator mounted mini-beam collimator: design, fabrication and dosimetric characterization", Physics in Medicine and Biology, Institute of Physics Publishing, Bristol GB, vol. 60, No. 17, Aug. 25, 2015, 15 pages.

* cited by examiner

FIG. 1A

PROTON BEAM
DELIVERY DEVICE
(END)

50

PATIENT

CONVERSION DEVICE FOR CONVERTING TREATMENT BEAM FOR TREATING LESION OF SUBJECT

CROSS-REFERENCE TO RELATED APPLICATIONS

This application is the National Stage filing under 35 U.S.C. 371 of International Application No. PCT/KR2022/008935 filed on Jun. 23, 2022, which claims the benefit of Korean Patent Application No. 10-2021-0096045 filed on Jul. 21, 2021, the contents of which are all hereby incorporated by reference herein in their entirety.

TECHNICAL FIELD

The present disclosure relates to a conversion device for converting a treatment beam for treating a subject's lesion.

BACKGROUND ART

Charged particle beams such as proton beams are used to treat lesions such as brain tumors.

During treatment, a large amount of radiation may be radiated to a patient's normal tissues in a proton beam's path so that the normal tissues are also affected by the radiation. For example, in the process of treating a patient's brain tumor with a proton beam, hair loss may be caused by the proton beam.

In particular, hair loss can have a very negative impact on the school and the social life of pediatric and female patients suffering from brain tumors, significantly reducing the quality of life of the patients.

DISCLOSURE

Technical Problem

The present disclosure is aimed at providing a conversion device for converting a treatment beam that allows normal tissues in the path of beams to be less affected by the beams during treatment using a charged particle beam such as a proton beam.

Technical Solution

The present disclosure may provide a conversion device for converting a treatment beam to treat a subject's lesion, including a collimator unit on which the treatment beam is incident and where a plurality of slits are formed; and a scattering unit that scatters the treatment beam that has passed through the collimator unit.

The treatment beam may include a charged particle bean.

The charged particle beam may include any one of a proton beam, a helium ion beam, and a carbon ion beam.

Each of the plurality of slits may extend long, the plurality of slits may be formed side by side, and the treatment beam may be spatially divided by the slit.

The treatment beam may be incident on the plurality of slits at different angles, and the direction in which one of the plurality of slits extends may be parallel to a corresponding incidence angle.

The distance in which the shortest one of the plurality of slits extends in the direction in which the treatment beam moves may be 1.5 to 10 times the longest depth to which the treatment beam penetrates.

The collimator unit may include first and second collimator units arranged in the direction in which the treatment beam moves.

The collimator unit may be made of either brass or tungsten.

The collimator unit may be concave toward the lesion.

The plurality of scattering units may have their respective levels of scattering, and it may be possible for a user to select any one of them.

The scattering unit may include a first scattering unit and a second scattering unit located between the first scattering unit and the lesion, and the first scattering unit and the second scattering unit may respectively include a plurality of scattering units having their respective levels of scattering.

The treatment beam that has passed through the scattering unit may irradiate the lesion, and the treatment beam may turn into an undivided beam in the lesion.

The scattering unit may include a metal plate.

The metal of the metal plate may have a density of 10 $g/cm^3$ to 25 $g/cm^3$.

The metal of the metal plate may include any one of lead, bismuth, and tungsten.

The treatment beam may be converted into spatially divided radiation for treatment while passing through the collimator and the scattering unit, and the conversion device may further include an absorption unit located between the scattering unit and the lesion and absorbing at least some of the radiation.

The absorption unit may be made of either a polymer with a density of 0.7 $g/cm^3$ to 2 $g/cm^3$ or a metal with a density of 2 $g/cm^3$ to 6 $g/cm^3$.

The total thickness of the air layer between the collimator unit and the absorption unit may be adjustable and may range from 1 cm to 8 cm.

The distance between the absorption unit and the lesion may be adjustable.

The conversion device may further include a range shifter that is located between a treatment beam delivery device for delivering the treatment beam and the collimator unit, allows the depth to which the treatment beam penetrates in the subject to become shallower, and is detachable.

The present disclosure provides a conversion device for converting a treatment beam to treat a subject's lesion, including a collimator unit that increases a PVDR of an incident treatment beam and allows the treatment beam remaining undivided to turn spatially divided; and a scattering unit that scatters the treatment beam that has passed through the collimator unit.

A plurality of slits may be formed in the collimator unit, and the PVDR of the treatment beam that has passed through the collimator unit may monotonically decrease depending on the depth to which the treatment beam penetrates.

The treatment beam that has passed through the scattering unit may be radiated to the lesion with the PVDR reduced to 1.0 to 1.2.

Advantageous Effects

The present disclosure provides a conversion device for converting a treatment beam that allows normal tissues to be less affected by beams during treatment using a charged particle beam such as a proton beam.

DESCRIPTION OF DRAWINGS

FIGS. 1A to 1C show how to use a conversion device according to the first embodiment of the present disclosure.

MODE FOR DISCLOSURE

Hereinafter, the present disclosure will be described in more detail with reference to the drawings.

The attached drawings are provided merely as examples to describe the technology of the present disclosure in more detail, and the technology of the present disclosure is not limited to the drawings. For explanation purposes, the thickness or the length of each part may be exaggerated in the appended drawings.

In the following embodiments of the present disclosure, the description is made by taking a proton beam as an example of treatment beams, but the treatment beam according to the present disclosure may be one of charged particle beams. The charged particle beam may be any one of a proton beam, a helium ion beam, and a carbon ion beam.

In addition, in the following embodiments, the description is made by taking a tumor in the brain as an example of lesions to be treated, but the position and the type of a lesion to be treated according to the present disclosure are not limited thereto.

Figure 1A:
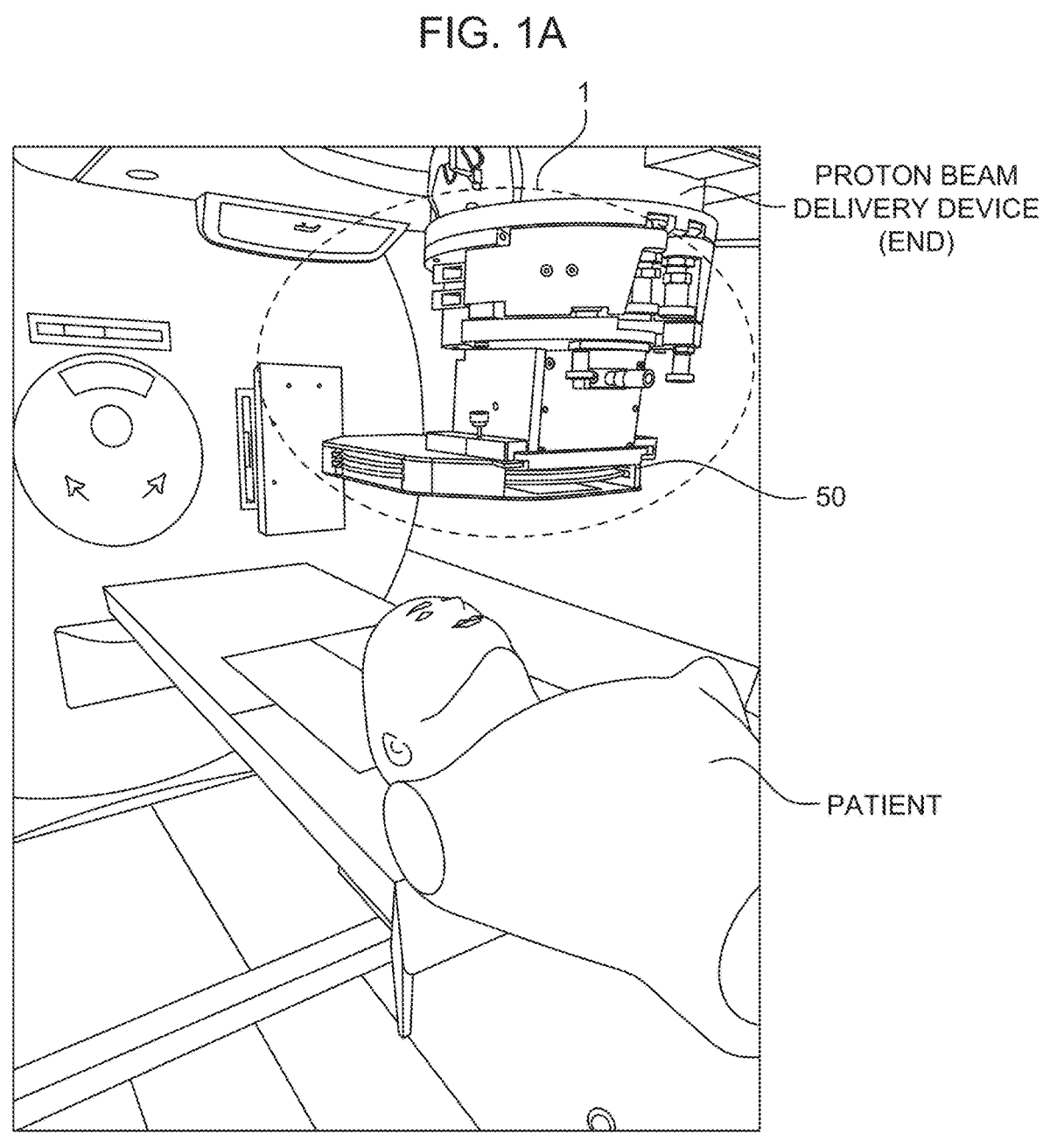
Figure 1B:
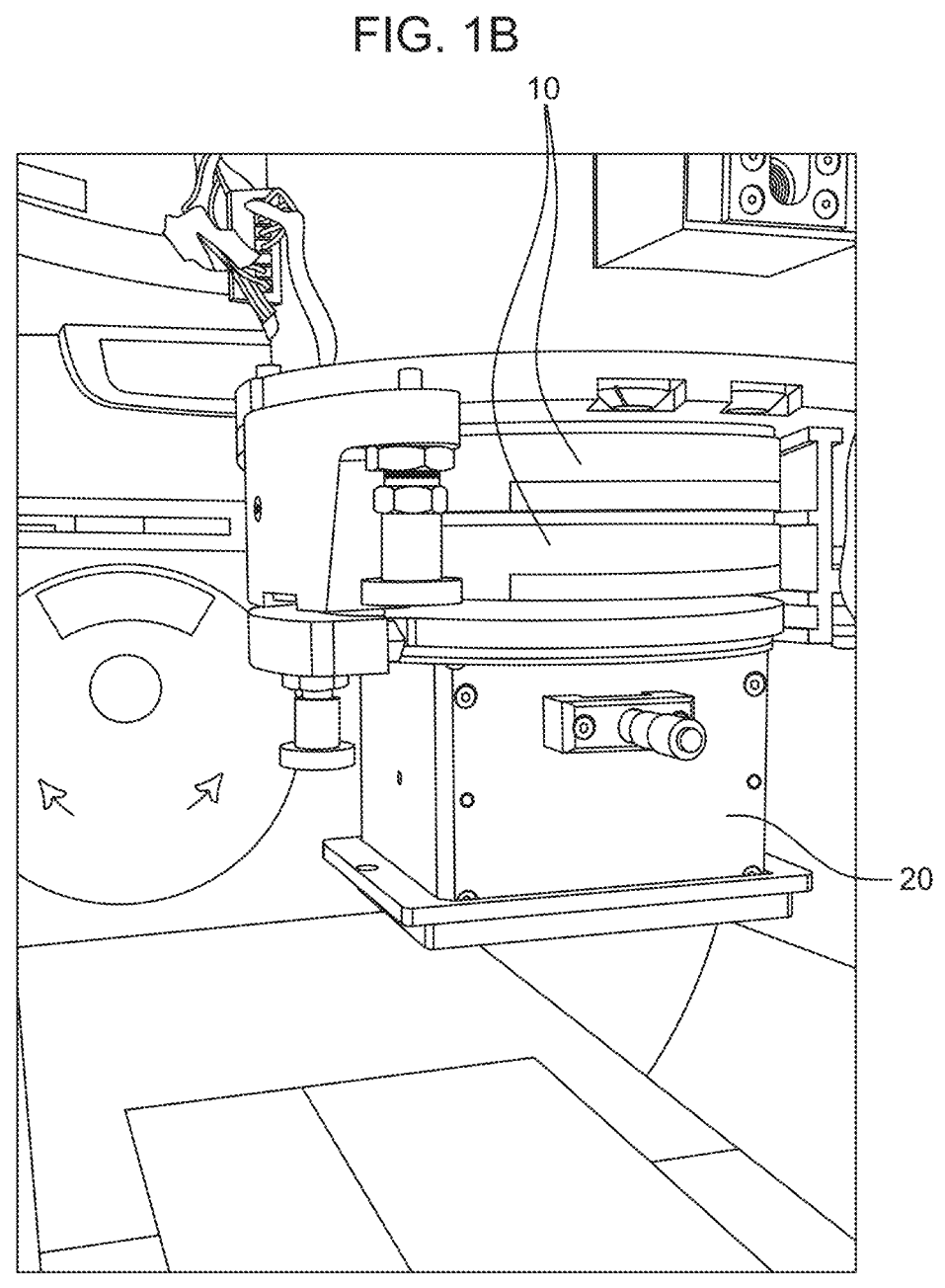
Figure 1C:
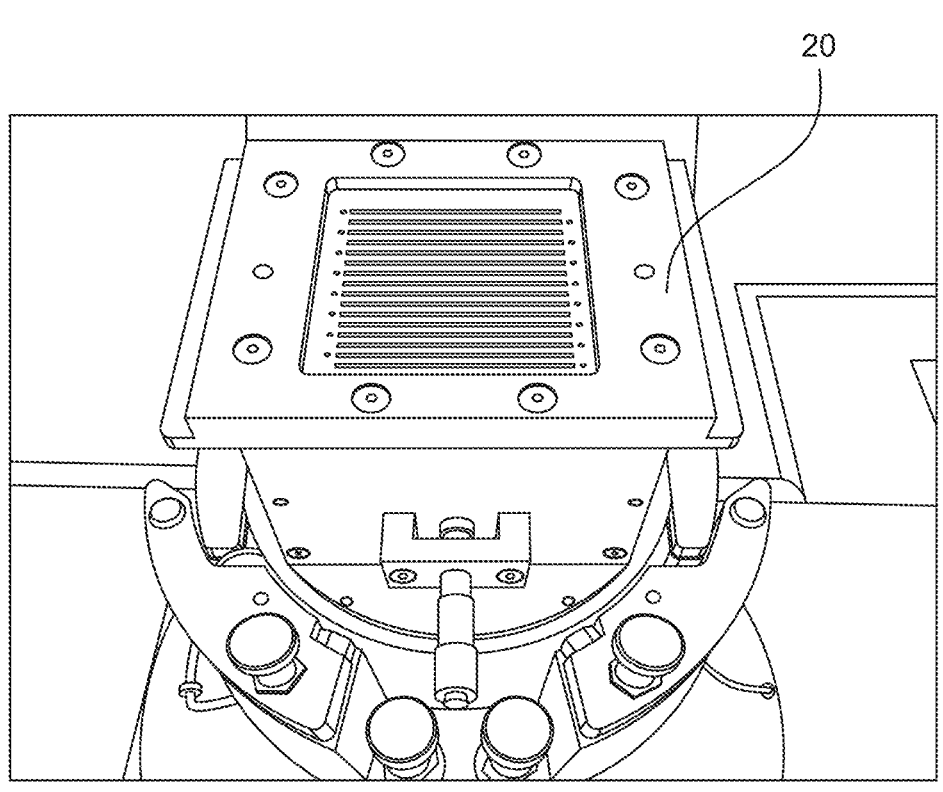

FIGS. 1A, 1B, and 1C show how to use a conversion device according to the first embodiment of the present disclosure.

The conversion device 1 may be used by being connected to the end of a proton beam delivery device for delivering a generated proton beam to a patient.

The proton beam delivery device may rotate by being connected to a gantry. A patient (subject) lies on a bed located at an extension of the proton beam delivery device, and a proton beam is radiated to the patient's lesion after passing through the conversion device.

The specific shape of the proton beam delivery device may change depending on the location of a lesion, etc., and a patient's posture may also change during treatment.

Figure 2:
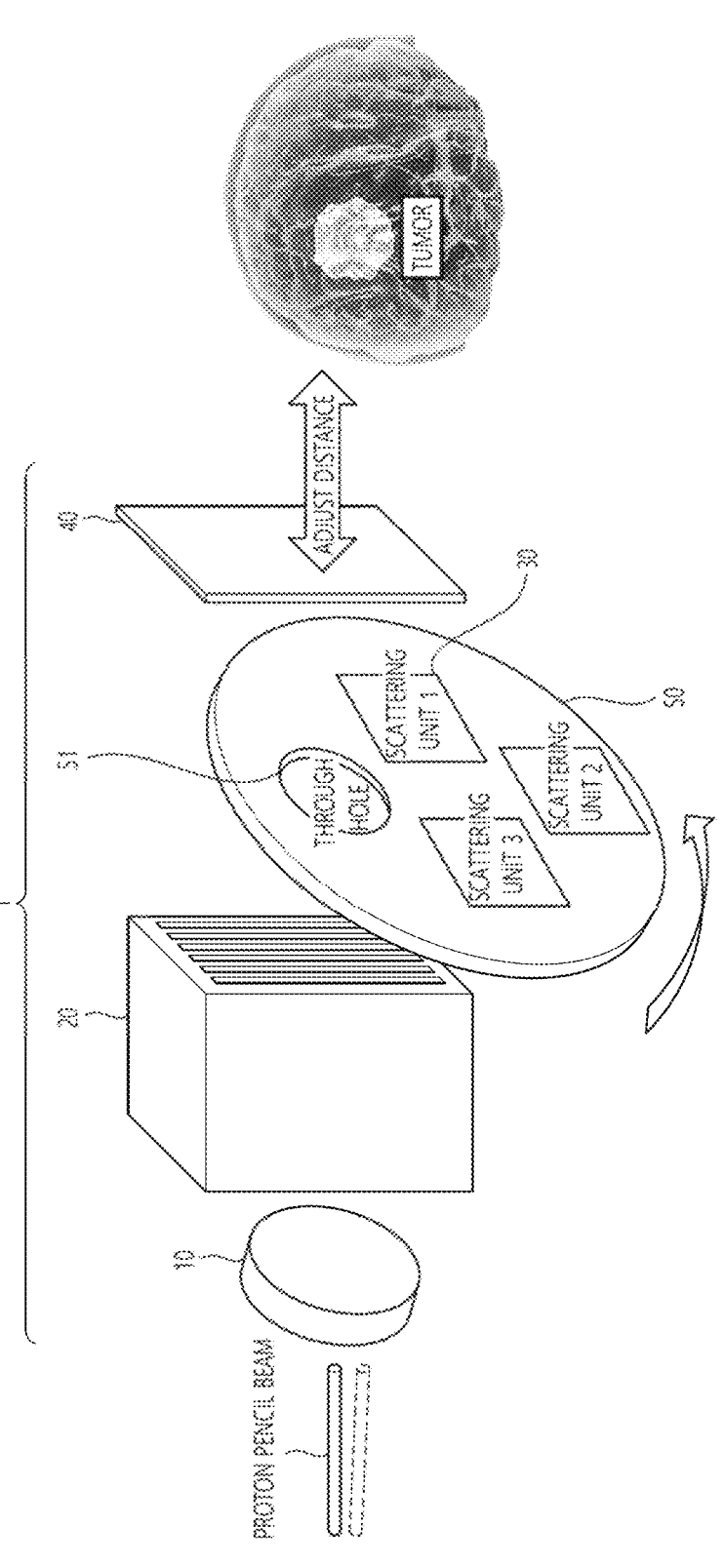
FIG. 2 shows the features of the conversion device according to the first embodiment of the present disclosure.

As shown in FIG. 2, the conversion device 1 may include a range shifter 10, a collimator unit 20, a scattering unit 30, an absorption unit 40, and a selection unit 50.

FIG. 2 does not show the feature of a case for accommodating each component, the feature of supporting each component in the case, the feature of adjusting the selection unit 50 from the outside, the feature of adjusting the distance between the components, etc.

In addition, FIG. 2 does not show the feature of coupling the conversion device 1 with the proton beam delivery device, and a person having ordinary skill in the art can appropriately select coupling feature.

The range shifter 10, the collimator unit 20, the scattering unit 30, and the absorption unit 40 may be sequentially arranged between the proton beam delivery device and a lesion, and a proton beam may be radiated to the lesion by sequentially passing through the range shifter 10, the collimator unit 20, the scattering unit 30, and the absorption unit 40.

A proton beam that has passed through the conversion device 1 may be radiated to a tumor, which is a lesion to be treated, by passing through a patient's scalp, skull, and normal brain.

Figure 3:
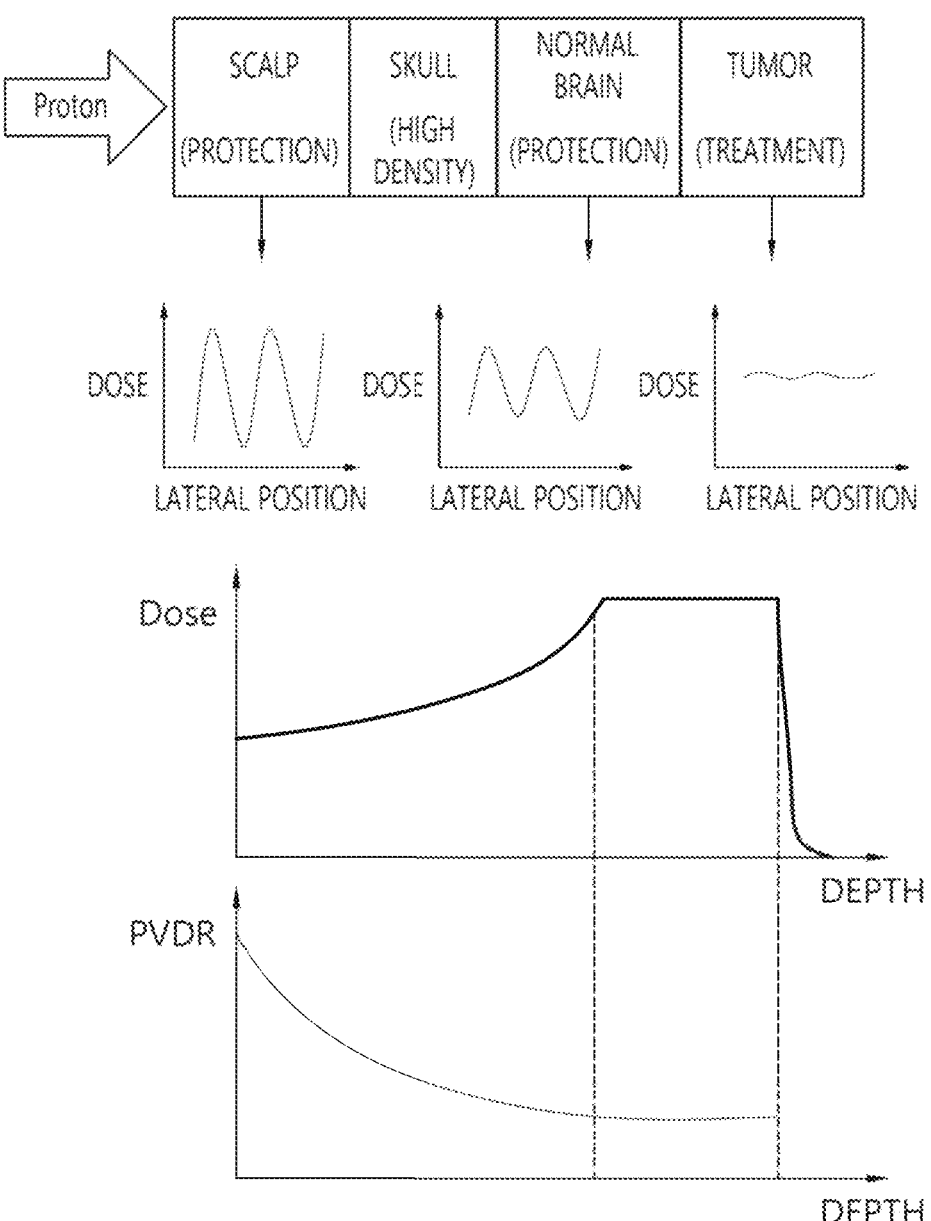
FIG. 3 shows how the dose shape of a proton beam changes by the conversion device according to the first embodiment of the present disclosure.

FIG. 3 shows how the dose shape of a proton beam changes as it sequentially passes from a patient's scalp to tumor.

A proton beam radiated to the scalp, which has to be protected from the proton beam, may be spatially divided, and the peak-valley dose ratio (PVDR) thereof may be high. The PVDR may be calculated by dividing Dp (dose at peak) by Dv (dose at valley).

In the present disclosure, "spatial division" means forming a spatially periodic dose distribution. The spatial division may be regarded as a state where the PVDR of a proton beam is greater than 1.1, greater than 1.2, or greater than 1.5, and actually 1.1 to 200, 1.2 to 200, or 1.5 to 200.

The PVDR of a proton beam incident on the scalp may be 3.0 to 100.

As a spatially divided proton beam passes through the scalp, the skull, and the normal brain, a low-dose area may be formed along the beam's path, so that normal tissue may be protected and, in particular, hair loss may be reduced.

Afterwards, after the proton beam has reached a lesion to be treated, the spatial division of the beam may be converted to undivided state, the low-dose area may disappear, and the PVDR may approach 1. The lesion may be treated effectively as the dose becomes constant. The PVDR of the proton beam radiated to the lesion may be 1.0 to 1.1 or 1.0 to 1.2.

As described above, according to the present disclosure, a state of high spatial division may be maintained in normal tissues, and a state of undivided may be maintained in tumors. As a result, normal tissues may be protected as much as possible, and tumors may be treated effectively.

Hereinafter, the conversion device according to the present disclosure will be described in detail with reference to FIGS. 4 to 9.

Figure 4:
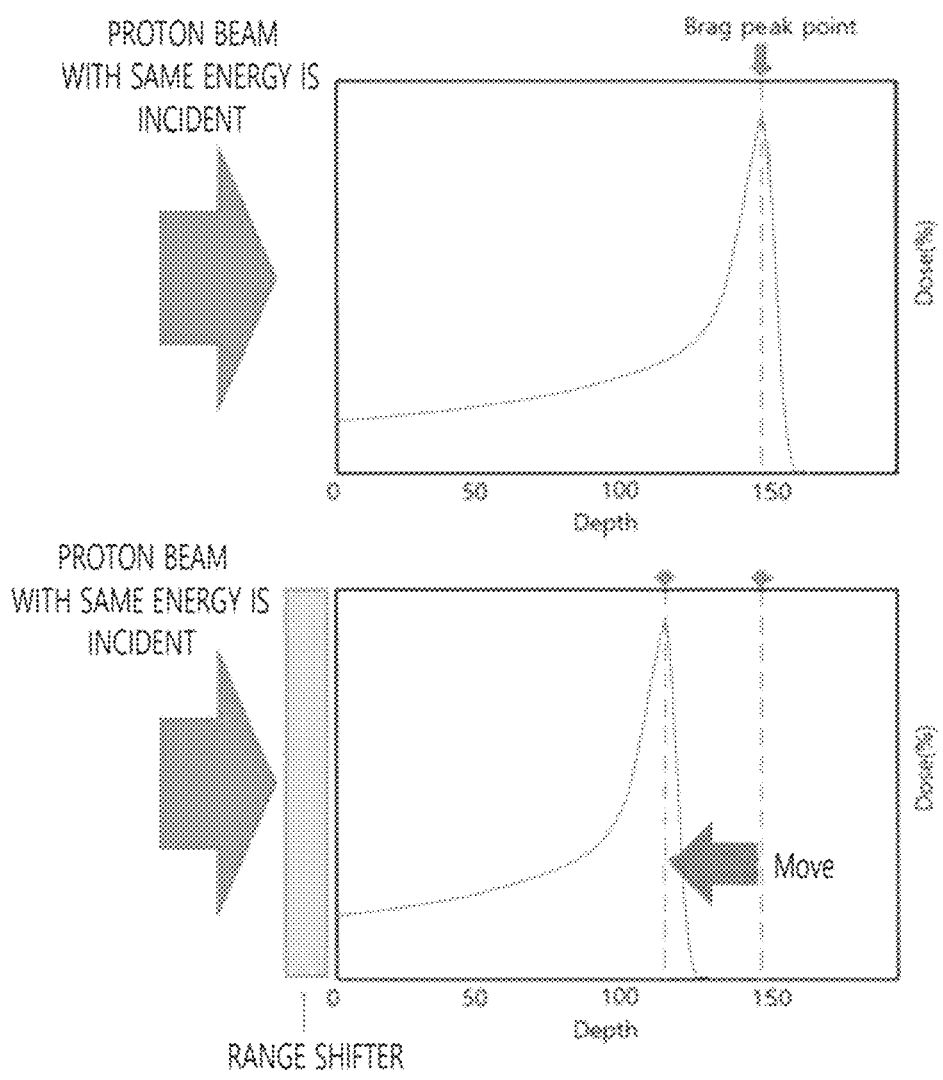
FIG. 4 is a view for illustrating how a depth of penetration of a proton beam changes by the range shifter of the conversion device according to the first embodiment of the present disclosure.
Figure 5:
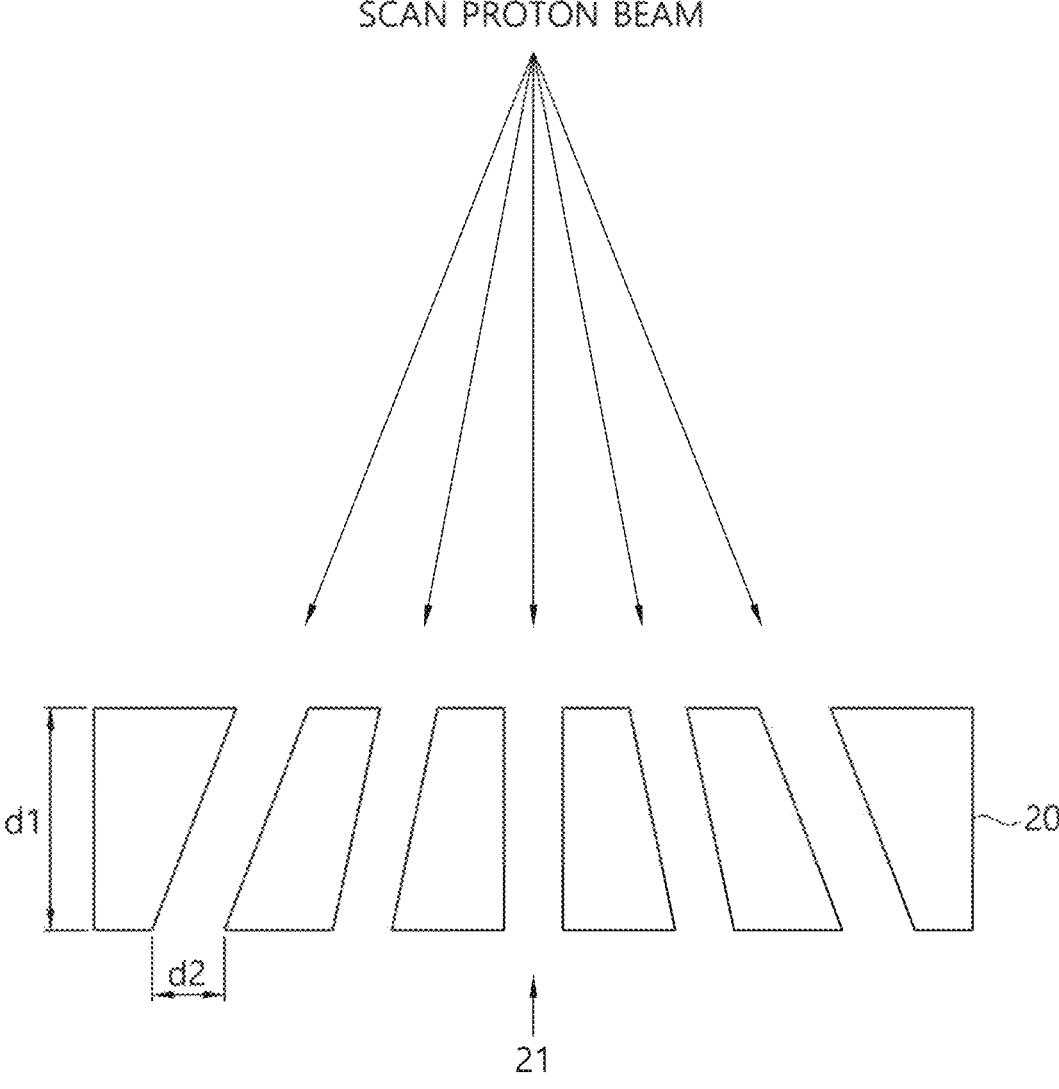
FIG. 5 shows a cross-section of the collimator unit of the conversion device according to the first embodiment of the present disclosure.
Figure 6:
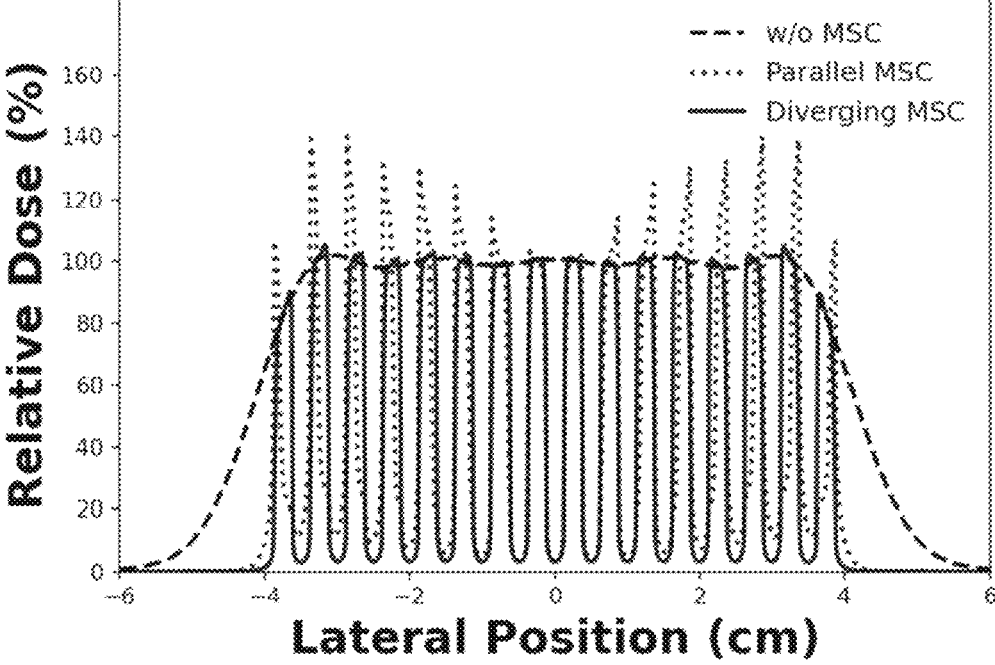
FIG. 6 shows the results of a computer simulation of how a lateral dose distribution changes depending on an angle of incidence of a beam and a direction of extension of a slit.
Figure 7:
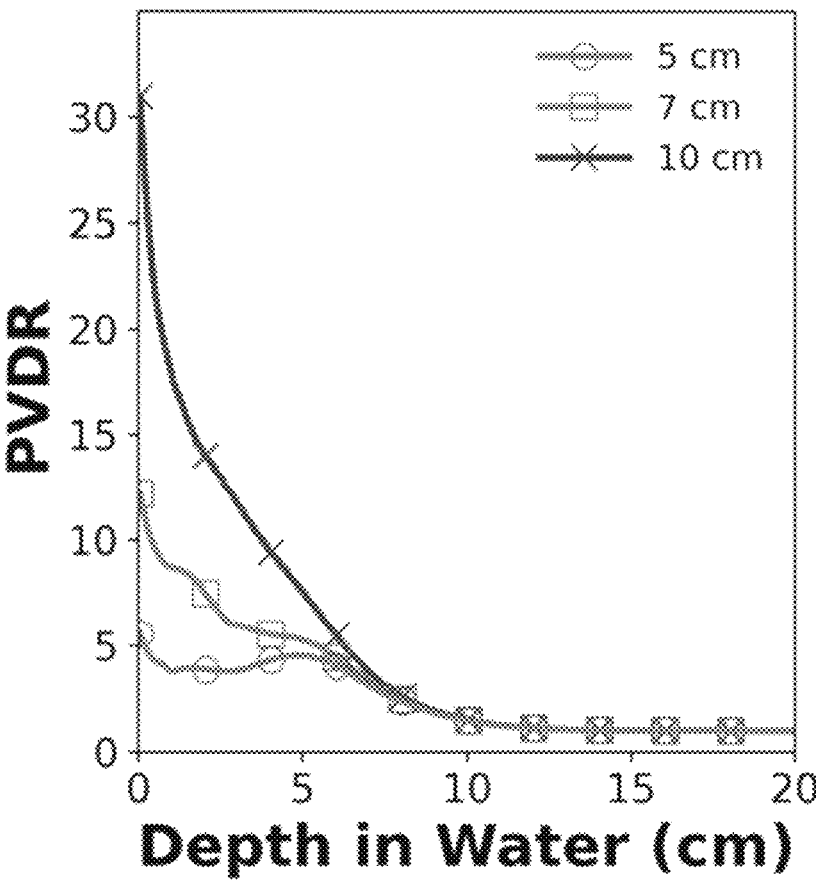
FIG. 7 shows the results of a computer simulation of how a PVDR changes depending on the depth of a medium for each thickness of the collimator unit.
Figure 8:
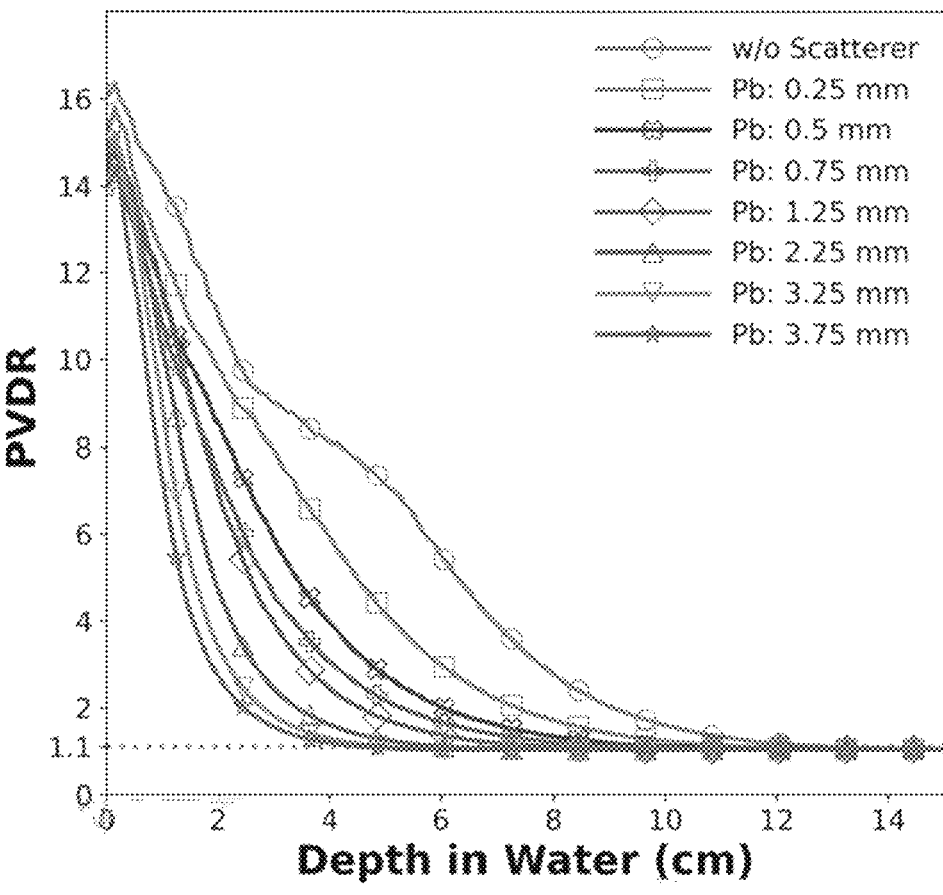
FIG. 8 shows the results of a computer simulation of how a PVDR changes depending on the depth of a medium for each thickness of a metal plate of the scattering unit.
Figure 9:
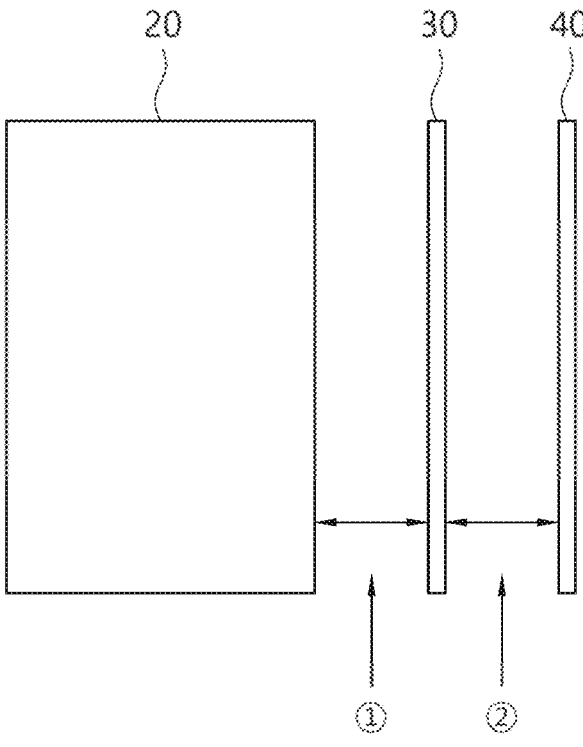
FIG. 9 shows the thickness of the air layer between the collimator unit and the absorption unit of the conversion device according to the first embodiment of the present disclosure.

FIG. 4 is a view for illustrating how a depth of penetration of a proton beam changes by the range shifter of the conversion device according to the first embodiment of the present disclosure, FIG. 5 shows a cross-section of the collimator unit of the conversion device according to the first embodiment of the present disclosure, FIG. 6 shows the results of a computer simulation of how a lateral dose distribution changes depending on an angle of incidence of a beam and a direction of extension of a slit, FIG. 7 shows the results of a computer simulation of how a PVDR changes depending on the depth of a medium for each thickness of the collimator unit, FIG. 8 shows the results of a computer simulation of how a PVDR changes depending on the depth of a medium for each thickness of a metal plate of the scattering unit, and FIG. 9 shows the thickness of an air layer of the conversion device according to the first embodiment of the present disclosure.

The range shifter 10 is placed between the proton beam delivery device and the collimator unit 20. The range shifter 10 may change the depth to which a proton beam penetrates in a subject, and, in particular, as shown in FIG. 4, the depth to which a proton beam penetrates in a patient's body may become shallower by the range shifter 10. The range shifter 10 may be made of a polymer material with a density of 0.7 $g/cm^3$ to 2 $g/cm^3$, and may be in the shape of a plate with a uniform thickness. The range shifter 10 may be provided to be detachable.

The collimator unit 20 may have a plurality of slits 21 formed therein. Each of the plurality of slits 21 may extend long and may be arranged side by side with each other.

The collimator unit 20 may spatially divide an incident proton beam and cause a PVDR to monotonically decrease based on the traveling distance in a subject.

The collimator unit 20 may be made of brass or tungsten.

As shown in FIG. 5, a proton beam may be incident on the collimator unit. 20 at a different angle for each of the plurality of slits 21. The direction in which each of the plurality of slits 21 extends may be parallel to the angle at which the proton beam is incident, that is, may be parallel to the incident proton beam scanned by a scanning magnet.

FIG. 6 shows the results of a computer simulation on the surface of a subject of how a lateral dose distribution changes depending on a beam incidence angle and a slit extension direction when a 161 MeV proton beam scanned by a scanning magnet is incident on two different types of collimator units.

As in the present disclosure, when an incidence angle and a slit's extension direction are parallel to each other (defocusing slit), the outline of the dose on the skin may be flat, and the dose distribution may be uniform even in lesions. In contrast, when an incidence angle and a slit extension direction do not match and slits are parallel to each other (parallel slit), the outline of the dose on the skin may not be flat but curved. In this case, the dose distribution may not be uniform even in lesions.

The distance d1 in which the shortest slit 21 extends, that is, the thickness of the collimator unit 20, may be 1.5 to 10 times the longest depth to which a proton beam penetrates. When the distance d1 is less than or equal to 1.5 times the longest depth to which a proton beam penetrates, it may be difficult to monotonically decrease a PVDR. When the distance d1 is equal to or more than 10 times the longest depth to which a proton beam penetrates, too much of the proton beam may be lost, so that treatment takes a very long time. In addition, in that case, a collimator may be difficult to handle.

According to another embodiment of the present disclosure, the width d2 of the slit 21 may increase toward the outside of a collimator.

FIG. 7 shows the results of a Monte Carlo computer simulation of how a PVDR changes depending on the depth of a medium while changing the extension length of a slit of a 200 MeV proton beam with the longest penetration depth of 4.52 cm in brass to 5, 7, and then 10 cm. It was assumed that a collimator unit made of brass was used and the medium was filled with water.

As shown in FIG. 7, a PVDR may begin to monotonically decrease when an extension length becomes 7 cm, which is approximately 1.5 times the longest penetration depth.

The scattering unit 30 may be made of a metal plate or may be made of a plurality of metal plates having different thicknesses.

Each scattering unit 30 may be mounted on the selection unit 50. The selection unit 50 may include a through hole 51, and a proton beam that has been spatially divided while passing through the collimator unit 20 may be incident on the through hole 51. It may be possible for a user to place the scattering unit 30 with a desired scattering level among a plurality of scattering units 30 in the through hole 51.

The scattering level of the scattering unit 30 may be adjusted by adjusting the material and/or the thickness of a metal plate. The metal plate may be made of a metal with a density of 10 to 25, and may be specifically made of any one of lead, bismuth, and tungsten.

The scattering unit 30 may allow a proton beam to be in a state of undivided based on the depth of a tumor. That is, the scattering unit 30 may determine a depth at which a PVDR of a spatially divided proton beam becomes lower than 1.2 or 1.1.

FIG. 8 shows the results of a Monte Carlo computer simulation of how a PVDR of a proton beam is adjusted depending on the depth of a medium for each thickness of a scattering unit made of lead.

In the computer simulation, the energy of the proton beam was 161 MeV, the width of the collimator made of brass was 2.5 mm, the width of the slits was 2.5 mm, the distance between the slits was 5 mm, and the extension length of the slits was 10 cm. It is assumed that the medium was filled with water.

FIG. 8 shows that the depth at which a PVDR reaches 1.1 may vary depending on the thickness of lead of a scattering unit.

The absorption unit 40 may be placed between the scattering unit 30 and a lesion and remove radiation generated or scattered by the range shifter 10, the collimator unit 20, the scattering unit 30, etc.

The absorption unit 40 may be made of either a polymer with a density of 0.7 $g/cm^3$ to 2 $g/cm^3$ or a metal with a density of 2 $g/cm^3$ to 6 $g/cm^3$. The metal used for the absorption unit 40 may be aluminum or titanium.

The sum of the thicknesses of the air layers between the collimator unit 20 and the absorption unit 40 may be adjustable and may be 1 cm to 8 cm. As shown in FIG. 9, the sum of the thicknesses of the air layers may be the sum of the distance (①) between the collimator unit 20 and the scattering unit 30 and the distance (②) between the scattering unit 30 and the absorption unit 40.

The uniformity of dose in a tumor may be controlled by controlling the sum of the thicknesses of the air layers. When the sum of the thicknesses of the air layers is increased, the uniformity of dose in the tumor may be improved. However, a PVDR of a proton beam radiated to the scalp may decrease.

It may be possible to adjust the distance between the conversion device 1 described above and a lesion.

Hereinafter, it will be described how to treat a patient using the conversion device according to the first embodiment of the present disclosure.

First, a treatment plan may be established by determining the position, the condition, etc. of a patient's lesion.

The treatment plan may include information on the maximum energy of a proton beam, the location of irradiation, treatment time, the selection of the conversion device 1, the location where the conversion device 1 will be placed, etc.

The components of the conversion device 1 may be selected for a proton beam to remain divided and turn undivided when reaching a lesion. The selection of the scattering unit 30 may be the most important, and, when selecting the scattering unit 30, whether to use the range shifter 10, the distance between the absorption unit 40 and a lesion, etc. may be taken into consideration.

After the conversion device 1 designed as desired is coupled with a device for generating a proton beam and a patient is placed, the proton beam may be radiated.

As the proton beam passes through the range shifter 10, the depth to which the proton beam penetrates in a patient's body may become shallower. Afterwards, as the proton beam may be spatially divided while passing through the collimator unit 20, the PVDR may decrease monotonically. As the proton beam is scattered while passing through the scattering unit 30, the depth at which the proton beam turns undivided may be determined. Afterwards, after scattered radiation is removed while the proton beam passes through the absorption unit 40, the proton beam may be incident on the patient.

A proton beam may remain divided and have a high PVDR of 1.2 or more in a patient's normal tissues, but may turn undivided and have a PVDR of 1.2 or less when reaching a lesion. As a result, it may be possible to reduce the influence of a proton beam on normal tissues and effectively treat lesions with the proton beam.

Hereinafter, the second to fourth embodiments of the present disclosure will be described with reference to FIGS. 10 to 12.

Figure 10:
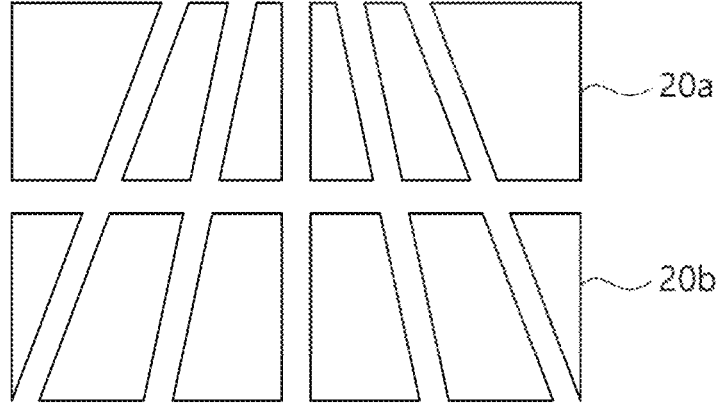
FIG. 10 shows a cross-section of the collimator unit of the conversion device according to the second embodiment of the present disclosure.

As shown in FIG. 10, according to the second embodiment of the present disclosure, the collimator unit 20 may include a first collimator 20a and a second collimator 20b. The first collimator 20a and the second collimator 20b may be arranged in the direction in which a proton beam is incident. According to another embodiment of the present disclosure, the collimator unit 20 may include three or more collimators made of different materials.

Figure 11:
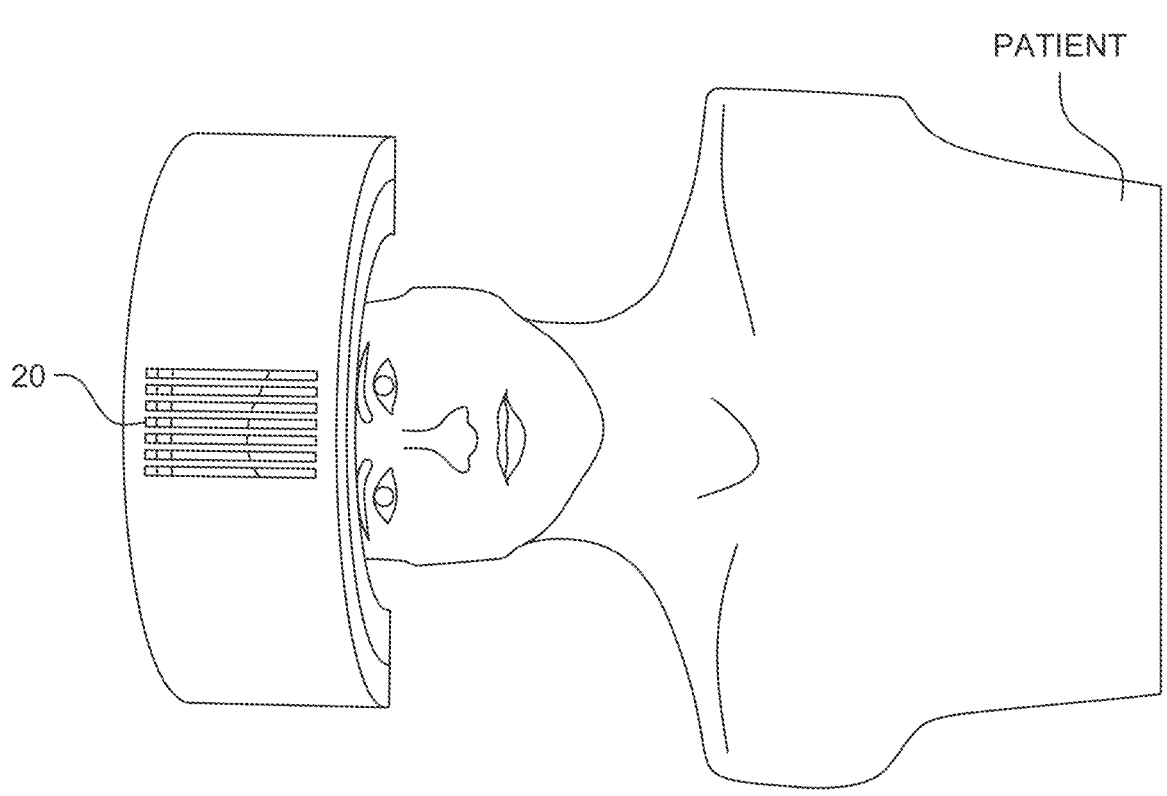
FIG. 11 shows the shape of the collimator unit of the conversion device according to the third embodiment of the present disclosure.

Referring to FIG. 11, the collimator unit 20 according to the third embodiment of the present disclosure may be curved and concave toward a patient.

Figure 12:
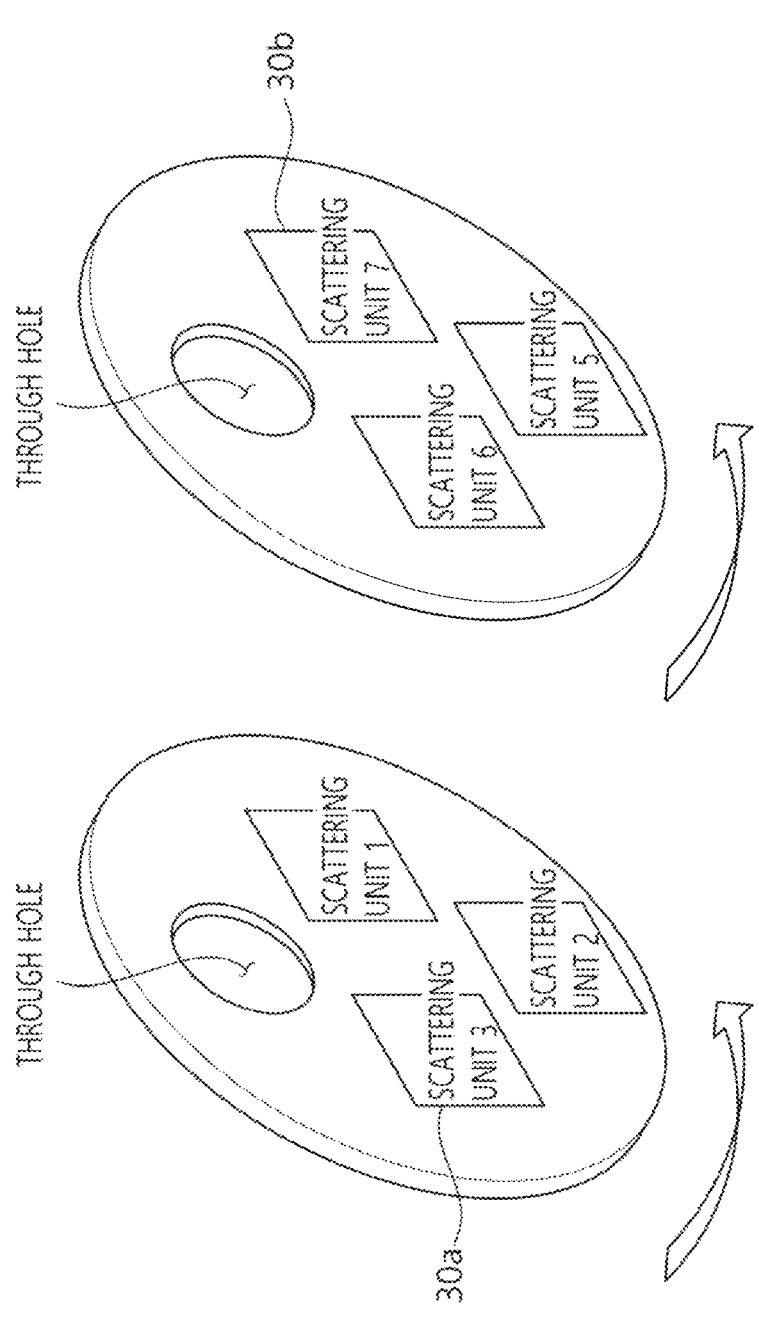
FIG. 12 shows the shape of the scattering unit according to the fourth embodiment of the present disclosure.

Referring to FIG. 12, according to the fourth embodiment of the present disclosure, the scattering unit 30 may include a first scattering unit 30a close to the collimator unit 20 and a second scattering unit 30b far from the collimator unit 20. A plurality of first scattering units 30a and second scattering units 30b may be provided. It may be possible for a user to vary the level of scattering by combining the first scattering unit 30a with the second scattering unit 30b to adjust the depth at which a proton beam turns undivided.

For example, when the first scattering unit 30a has metal plates with a thickness of 10 mm, 20 mm, and 30 mm, respectively, and the second scattering unit 30b has metal plates with a thickness of 3 mm, 5 mm, and 7 mm, respectively, it may be possible for a user to use metal plates with a thickness of 10 mm, 13 mm, 15 mm, 17 mm, 20 mm, etc., respectively, by combining the two scattering units.

The first scattering unit 30a and the second scattering unit 30b may be spaced apart from each other, and, in this case, the total thickness of the air layer according to the fourth embodiment may include the distance between the first scattering unit. 30a and the second scattering unit 30b.

The above-described embodiments are examples for describing the present disclosure, and the present disclosure is not limited thereto. A person having ordinary skill in the technical field to which the present disclosure belongs would be able to carry out the present disclosure by making various modifications to the above-described embodiments, so the scope of the technology of the present disclosure should be determined by the appended claims.

The invention claimed is:

1. A conversion device for converting a treatment beam to treat a subject's lesion, comprising:
a collimator unit on which the treatment beam is incident and in which a plurality of slits are formed, wherein the treatment beam includes a charged particle beam; and
a scattering unit that scatters the treatment beam that has passed through the collimator unit, wherein the scattering unit includes a first scattering unit and a second scattering unit located between the first scattering unit and the lesion, and the first scattering unit and the second scattering unit respectively include a plurality of scattering units having respective levels of scattering and being selectable by a user.

2. The conversion device of claim 1, wherein the charged particle beam includes any one of a proton beam, a helium ion beam, and a carbon ion beam.

3. The conversion device of claim 1, wherein each of the plurality of slits extends in a predetermined direction, the plurality of slits are formed side by side, and the treatment beam is spatially divided by the plurality of slits.

4. The conversion device of claim 3, wherein the treatment beam is incident on the plurality of slits at different angles, and the direction in which the plurality of slits extends is parallel to a corresponding incidence angle.

5. The conversion device of claim 1, wherein a distance in which a shortest slit of the plurality of slits extends in a direction in which the treatment beam moves is 1.5 to 10 times a longest depth to which the treatment beam penetrates.

6. The conversion device of claim 5, wherein the collimator unit includes first and second collimator units arranged in the direction in which the treatment beam moves.

7. The conversion device of claim 1, wherein the collimator unit is made of either brass or tungsten.

8. The conversion device of claim 1, wherein the collimator unit is concave toward the lesion.

9. The conversion device of claim 1, wherein the treatment beam that has passed through the scattering unit irradiates the lesion, and the treatment beam turns into an undivided beam in the lesion.

10. The conversion device of claim 1, wherein the scattering unit includes a metal plate.

11. The conversion device of claim 10, wherein a metal of the metal plate has a density of 10 $g/cm^3$ to 25 $g/cm^3$.

12. The conversion device of claim 11, wherein the metal of the metal plate includes any one of lead, bismuth, and tungsten.

13. The conversion device of claim 1, wherein the treatment beam is converted into spatially divided radiation for treatment while passing through the collimator unit and the scattering unit, and
wherein the conversion device further comprises an absorption unit located between the scattering unit and the lesion and absorbing at least some of the radiation.

14. The conversion device of claim 13, wherein the absorption unit is made of either a polymer with a density of 0.7 g/cm$^3$ to 2 g/cm$^3$ or a metal with a density of 2 g/cm$^3$ to 6 g/cm$^3$.

15. The conversion device of claim 13, wherein a total thickness of an air layer between the collimator unit and the absorption unit is adjustable and ranges from 1 cm to 8 cm.

16. The conversion device of claim 13, wherein a gap between the absorption unit and the lesion is adjustable.

17. The conversion device of claim 2, further comprising a range shifter that is located between a treatment beam delivery device for delivering the treatment beam and the collimator unit, allows a depth to which the treatment beam penetrates in the subject to become shallower, and is detachable.

* * * * *